United States Patent [19]

Reitz et al.

[11] Patent Number: 5,290,948
[45] Date of Patent: Mar. 1, 1994

[54] PROCESS FOR PRODUCING POLYHYDROXYLATED PIPERIDINES AND PYRROLIDINES AND COMPOUNDS THEREOF

[75] Inventors: Allen B. Reitz; Ellen W. Baxter, both of Lansdale; Bruce E. Maryanoff, Solebury Township, Bucks County, all of Pa.

[73] Assignee: McNeilab, Inc., Spring House, Pa.

[21] Appl. No.: 583,615

[22] Filed: Sep. 17, 1990

[51] Int. Cl.$^5$ ............................................ C07D 233/54
[52] U.S. Cl. ..................................... 548/541; 548/542
[58] Field of Search ................................ 548/541, 542

[56] References Cited

U.S. PATENT DOCUMENTS 4,910,320  3/1990  Inoue et al. .......................... 548/541
4,966,901  10/1990  Zoller et al. ......................... 548/541

FOREIGN PATENT DOCUMENTS 1505241  12/1967  France ................................. 548/541
667923  3/1952  United Kingdom ................ 548/541

OTHER PUBLICATIONS

Chemical Abstract, vol. 103 No. 156296g, Bello et al, 1985, "Inhibition of human α& β-D glucosidases and xypyrrolidine."

*Primary Examiner*—C. Warren Ivy
*Assistant Examiner*—Raymond Covington
*Attorney, Agent, or Firm*—Ralph R. Palo

[57] ABSTRACT

A process for converting 1,4- and 1,5-dicarbonyl sugars to pyrrolidine and piperidine amino sugars. Novel compounds resulting from this process are also described.

13 Claims, No Drawings

PROCESS FOR PRODUCING POLYHYDROXYLATED PIPERIDINES AND PYRROLIDINES AND COMPOUNDS THEREOF

BACKGROUND IN THE INVENTION

Many polyhydroxylated piperidines and pyrrolidines are powerful inhibitors of glycohydrolases, enzymes responsible for glycoprotein processing and the gastrointestinal breakdown of dietary carbohydrates. See, for example, Fleet, G. W. *J. Chem. Brit.*, 1989, 287; Fellows, L. E. *Chem. Brit.*, 1987, 842. These azasugars have potential therapeutic utility in the treatment of various diseases, such as diabetes, cancer and viral infections. Particular attention has focused on anti-HIV activity in the AIDS area. Therefore, the syntheses of polyhydroxylated piperidines and pyrrolidines such as 1-deoxynojirimycin, an antiviral agent, has been the subject of considerable recent research. Bayer, for example, is developing miglitol, a polyhydroxylated piperidine, which is useful as an anti-diabetic agent, *Drugs Fut.* 1986, 11, 1039.

Synthetic routes to azasugars have commonly entailed processes such as azide displacement/reduction and N-alkylative cyclization with extensive protecting-group manipulation. See, for example, (a) Paulsen, H,.; Sangster, I.; Heyns, K. *Chem. Ber,* 1967, 100, 802. (b) Inouye, S. et al. *Tetrahedron* 1968, 23, 2125. (c) Saeki, H.; Ohki, E. *Chem. Pharm. Bull.* 1968, 11, 2477. (d) Kinast, G.; Schedel, M. *Angew. Chem. Int. Ed. Engl.* 1981, 20, 805. U.S. Pat. No. 4,266,025; May 1981. (e) Vasella, A.; Voeffray, R. *Helv. Chim. Acta* 1982, 65, 1134 (f) Koebernick, W.; E. P. 55-431; U.S. Pat. No. 4,611,058; Sep. 9, 1986; assigned to Bayer AG. (g) Bernotas, R.; Ganem, B. *Tetrahedron Lett.* 1985, 26, 1123. (h) Setoi, H.; Takeno, H.; Hashimoto, M. *Chem. Pharm. Bull.* 1986, 34, 2642. (i) Broxterman, H. J. G. et al. *Rec. Trav. Chim. Pays-Bas* 1987, 106, 571. (j) Fleet, G. W. J.; Fellows, L. E.; Smith, P. W. *Tetrahedron* 1987, 43, 979. (k) Iida, H.; Yamazaki, N.; Kibayashi, C. *J. Org. Chem.* 1987, 52, 3337. (l) Ziegler, T.; Straub, A.; Effenberger, F. *Angew; Chem. Int. Ed. Engl.* 1988, 27, 716. (m) Schmidt, R. R.; Michel, J.; Rucker, E. *Liebigs Ann. Chem.* 1989, 423. (n) Chida, N.; Furuno, Y.; Ogawa, S. *J. Chem. Soc., Chem. Commun.* 1989, 1230. (o) Beaupere, D.; Stasik, B. et al. *Carbohydr. Res.* 1989, 191, 163. (p) von der Osten, C. H. et al. *J. Am. Chem. Soc.* 1989, 111, 3924. (q) Ikota, N. *Heterocycles* 1989, 22, 1469. (r) Tsuda, Y.; Okuno, Y.; Iwaki, M.; Kanemitsu, K. *Chem. Pharm Bull* 1989, 37, 2673. (s) Fleet, G. W. J. et al. *Tetrahedron Lett.* 1990, 31, 490. (t) Anzeveno, P. B., Creemer, L. J. *Tetrahedron Lett.* 1990, 31, 2085 (u) Dax, K. et al. *J. Carbohydr. Chem.* 1990, 9 479. Certain of the semi-synthetic methods employing a key enzymatic transformation have proved to be useful.

U. S. Patent No. 4,611,058 describes high stereoselectivity in the intramolecular reductive amination of 6-amino-6-deoxy-L-sorbose when using a borohydride reducing agent. U. S. Pat. Nos. 4,806,650 and 4,266,025 describe additional Bayer processes involving the production of 1-deoxynojirimycin. The first patent describes the microbial oxidation portion of the process together with the intramolecular reductive amination. The second patent describes the overall process containing the catalytic reduction of the imine with a palladium on carbon catalyst. The processes for the production of 1-deoxynojirimycin are expensive to run because of the number of chemical steps involved and/or the need for purification of the intermediates or targets. Many of the known processes involve a cyclization step that is not stereoselective resulting in the need for tedious separations.

Piperidines and pyrrolidines have been prepared by double reductive amination of dicarbonyl compounds with an amine and $NACNBH_3$ (Borch, R. F. et al. *J. Am. Chem. Soc.* 1971, 22, 2897), but this reaction has not been applied to the preparation of aminosugars from dicarbonyl sugar starting materials.

The present invention involves a synthesis process for amino sugars that is efficient and economic. In particular, the process described is more concise and stereospecific in comparison with the processes for some of the preparations of amino sugars known in the prior art.

SUMMARY OF THE INVENTION

The present invention is directed to a synthetic process whereby 1,4- or 1,5-dicarbonyl sugars are reacted with an amine, protonated with an acid, and a source of hydride to produce pyrrolidine or piperidine amino sugars. In this manner, the crucial skeleton of the amino sugar is prepared in a single step. Certain of the resulting amino sugars have been found to inhibit glycosidase enyzmes and thus may have potential in a number of different therapeutic areas such as in the treatment of diabetes, cancer and viral infections. Some of these compounds also exhibit anti-HIV activity.

DETAILED DESCRIPTION OF THE PREFERRED EMBODIMENT

The process of the present invention is directed to the synthesis of compounds of the following formula (I) and stereoisomers thereof:

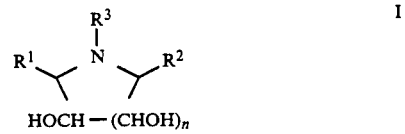

wherein $R^1$ and $R^2$ are the same or different and selected from $CH_2OH$, $CH_3$, H, and $CH_2F$. $R^3$ is H, straight or branched $C_1$-$C_{20}$ alkyl, which may be substituted with one or more heteroatoms such as hydroxy, $C_1$-$C_{20}$ alkoxy, $C_6$-$C_{10}$ aryloxy, thio, carboxy, or $C_1$-$C_{20}$ dialkylamino. $R^3$ may also be $C_7$-$C_{30}$ aralkyl such as benzhydryl, $C_3$-$C_{10}$ heteroaryl, $C_1$-$C_{10}$ alkyl amino, $C_3$-$C_{12}$ aryl amino, amino, $C_1$-$C_{10}$ alkyloxy, $C_7$-$C_{20}$ aralkyl oxy, phenyl, or phenyl substituted with one or more of $C_1$ to $C_6$ alkyl, $C_1$ to $C_6$ alkoxy, halogen, carboxy, thio, or $C_1$-$C_6$ alkylthio, n=1 or 2. Phenyl and Ph are used interchangeably herein.

Notwithstanding the foregoing description of $R^3$, $R^3$ cannot be a group wherein the carbon atom attached to the ring nitrogen is a quaternary carbon. As defined herein a quaternary carbon is one having all of its bonds to elements other than hydrogen. The reason for this limitation is that the $R^3$ substituent is added by the reaction of a starting compound with an amine having the $R^3$ substituent thereon. It is presently believed that steric hindrance resulting from a quaternary $R^3$ substituent will prevent the reaction from occurring.

The synthesis process comprises reacting a compound of the following formula II:

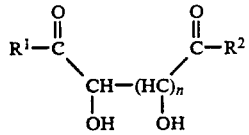

wherein n is 1 or 2, with an amine of the formula $R^3NH_2$ in the presence of an acid and a source of hydride to produce a compound of the formula I and isomers thereof:

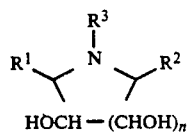

Examples of amines suitable for carrying out the process of the present invention include ammonia, hydrazine, benzhydrylamine, n-butylamine, 2-hydroxyethyl amine, benzylamine and aniline. Amines with greater than 12 carbon atoms such as benzhydrylamine generally result in products that are not very soluble in water and thus can be extracted into an organic solvent such as chloroform or methylene chloride. When amines with less than 12 carbon atoms are employed the resulting products are generally water soluble initially and are treated with an ion exchange resin such as Dowex ® 50W-X8 resin, which adheres the products on the resin allowing for the removal of non basic materials. The products are liberated from the resin by treatment with $NH_4OH$. The only primary amines which were found not to work are those bearing a quaternary carbon atom such as trityl or adamantyl amine. As alluded to previously, it is believed that steric hindrance prevents the reaction from proceeding in the manner described. The amine is generally present in a molar ratio of amine to sugar of from about 0.5 to 2.0, and most preferably in an amount of about 0.8 to 1.0.

Any suitable hydride source may be employed, although it is presently preferred to use a borohydride and more preferably a complex borohydride. Suitable borohydrides include $NACNBH_3$, $nBu_4NCNBH_3$ and catecholborane. The molar ratio of hydride source to the starting sugar in generally of from about 0.67 to 10.0, more preferably of from about 1.0 to 5.0 and most preferably of from about 1.0 to 3.0.

An acid is employed in the reaction to protonate the amine. Suitable acids include mineral acids such as HCl, HBr, and HI, and organic acids such as acetic acid, benzoic acid, fumaric acid, maleic acid, succinic acid, and oxalic acid. The acid is generally present in an amount of about a molar ratio 1 part acid to 1 part amine, or slightly more in order to keep the pH of the reaction at between 5 and 7.

The synthesis is carried out in a suitable medium, preferably water and/or alcohol solvent. When using an alcohol solvent it is presently preferred to employ an alcohol having 1–4 carbon atoms. The synthesis is conducted at a temperature of from about $-78°$ C. to 100° C. and more preferably of from about 0° C. to 80° C. The precise temperature employed will depend on the solubility of the starting sugar and the rate of reaction. The pH is maintained at about 5 to 7.

After the reaction is complete, the products are isolated by a combination of an ion-exchange or extractive work-up followed usually by chromatography on silica gel. The reaction is typically stereoselective. In cases where significant stereocontrol is realized, it is believed that the hydride is directed by of one or more proximal hydroxyls. Stereochemistry can be determined by inspection of the spectral properties of the products, especially by examination of their H-1 and C-13 NMR spectra.

If the reductive amination is performed with ammonia, protonated with a suitable acid, the product is itself the aminosugar without any additional non-hydrogen groups attached to the hydroxyls or ring nitrogen. However, if a primary amine is employed in the reductive amination, the resulting product bears a pendant $R^3$ group, other than H, on the ring nitrogen. Certain of the $R^3$ groups can be removed by further chemical manipulations known in the art as hydrogenolysis and/or solvolysis. The hydrogenolysis reaction is normally carried out with hydrogen in the presence of a suitable catalyst such as palladium on carbon or platinum. The hydrogen for this reaction may be obtained from any suitable source including ammonium formate in a transfer hydrogenation. If the amine reactant in the double reductive amination is hydrazine or a 1,1-dialkyl or 1,1-diaryl hydrazine, the products themselves are hydrazines. Hydrogenolysis of the N-N bond would then produce the aminosugars with a hydrogen on the nitrogen.

While many dicarbonyl sugars are known compounds, their preparation is at times tedious and time consuming. The present invention also includes a modified process for producing a 1,5-dicarbonyl sugar of the formula (V)

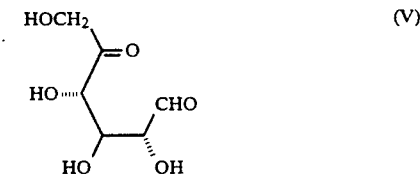

The new and improved two step process, which is described in detail in Example 1 is represented by the following general reaction scheme:

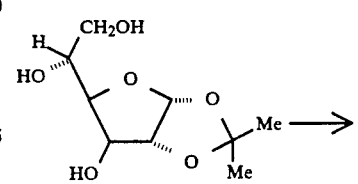

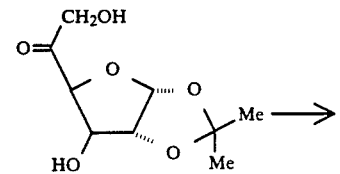

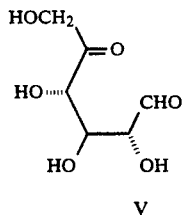

V

The first step of this reaction is a selective oxidation using bromine and dibutyltin oxide. The resultant product of the formula IV is then heated in the presence of an ion exchange resin such as a polystyrene based resin having sulfonic acid residues. Dowex ® 50W-X8 resin is a particularly preferred resin. Thereafter the suspension of resin and product is cooled, the resin is removed and the product of formula V is thereby isolated. An example of the preparation of a six member ring amino sugar according to the present invention using the dicarbonyl sugar of formula V is as follows:

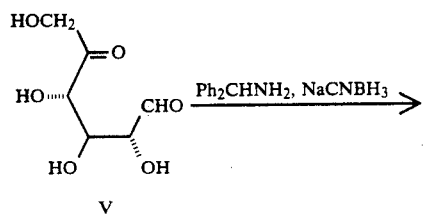

wherein Ph is phenyl. This reaction is described in detail in Example 2.

Depending upon the final product desired the substituent on the ring nitrogen can be removed by hydrogenolysis according to the following reaction:

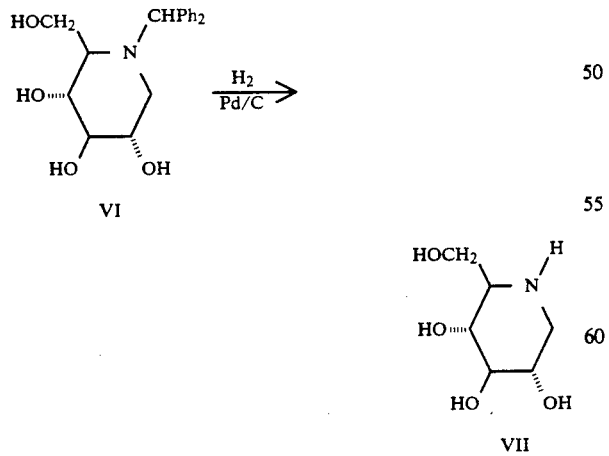

The hydrogenolysis is generally carried out in the presence of a precious metal catalyst such as in Pd(OH)$_2$/C and H$_2$, 10% Pd/C and H$_2$, and NH$_4$HCO$_2$ and 10% Pd/C. This hydrogenolysis is exemplified in Example 3.

One stereoisomer, the compound of the formula VI was the major one formed in the reaction of the compound of formula V with benzhydrylamine. Only minor amounts of the other isomer (ca. 4%) were obtained. A similar stereochemical outcome was seen in the reaction of the compound of formula V with 2,2-diphenylethylamine (as described in Example 4). The reaction of the compound of formula V with 1,1-diphenylhydrazine produced a 3:2 ratio of the glucitol: iditol stereoisomers of the formulas:

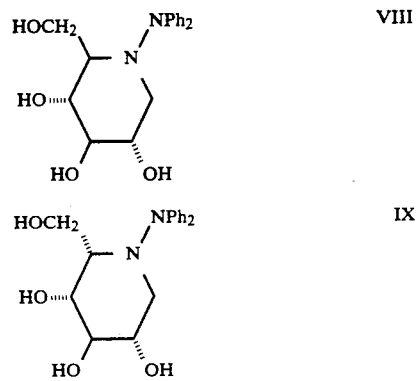

This reaction is described in Example 5.

An example of a reaction resulting in a five membered ring amino sugar is as follows:

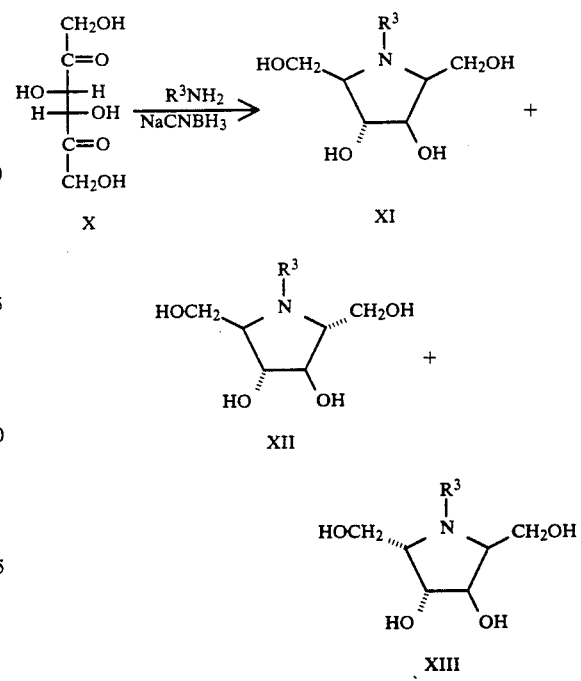

A specific example of this reaction is described in Example 6, wherein benzhydrylamine (R$^3$=Ph$_2$CH) is the reactant. In that Example isomers XI, XII and XIII were produced in a ratio of 86:6:8. Isomers XI and XII in that Example could then be isolated by conventional techniques described in Examples 6 and 7.

Depending upon the desired end product and the nature of R$^3$ the substituent on the ring nitrogen can be removed by hydrogenolysis according to the following reaction showing this reaction for XI (R₃=Ph₂ CH):

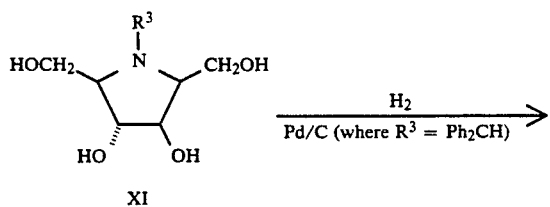

XI

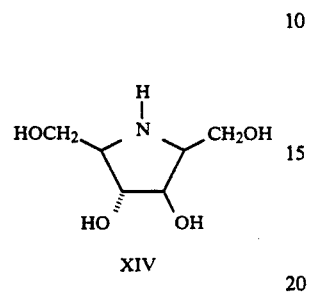

XIV

Example 8 describes this reaction in detail.

Compound XIV may be further reacted with an electrophile such as cinnamyl chloride, 2-(4-methoxyphenyl)ethyl chloride, nBuBr, or 2-benzdioxolanyl-methyl bromide in the presence of a base such as triethyl amine, potassium carbonate, sodium carbonate, diisopropyl ethyl amine to produce an N-alkyated derivative of the aminosugar. A few of such compounds demonstrate biological activity. Such a reaction is generally represented by the following:

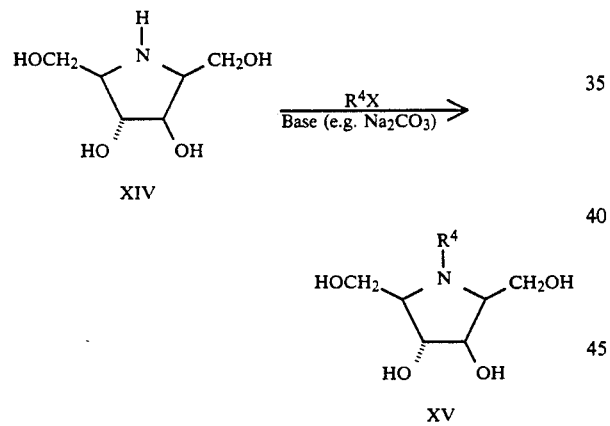

wherein $R^4$ is any of alkyl, aralkyl, dialkylamino alkyl or alkoxy- or hydroxy-alkyl and X is any of Cl, Br, I, tosylate, or mesylate. A specific example is shown in Example 9 using 2-(4-fluorophenoxy)ethyl bromide as the reactant.

When compound X was reacted with 4-fluoroaniline, a mixture of three stereoisomers of the formulas:

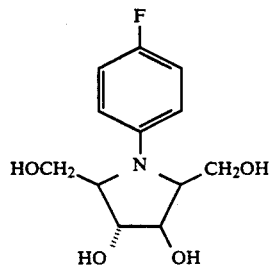

XVI

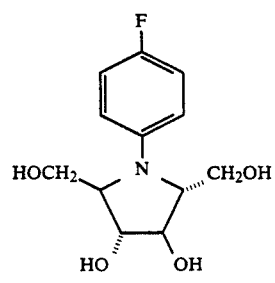

XVII

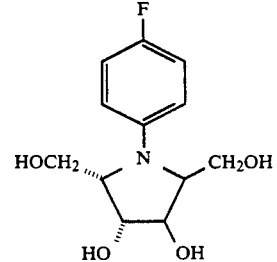

XVIII were produced in a ratio of 45:40:15. Further details of this reaction are shown in Example 10.

Specific examples of five membered ring compounds that can be produced according to the present invention are shown in Table 1.

TABLE 1

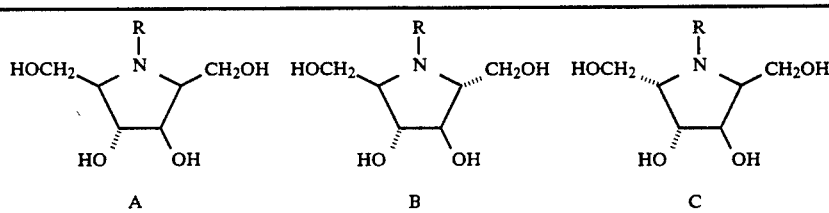

| Structure | R | Inh. of Maltase(Sucrase) (%, at 100 mM) | HIV1/HIV2 Act. |
|---|---|---|---|
| 1. A | Ph₂CH | 0(0)[1] | Weak anti-HIV1 act. |
| 2. A | H | 0(0)[2] | No anti-HIV1 act. |
| 3. B | Ph₂CH | 0(0) | No anti-HIV1 act. |
| 4. A:B 93/7 | S-(Me)CHPh | NT[3] | NT |
| 5. A | 9-Fluoroenyl | NT | NT |
| 6. A:B 88/12 | CH₃(CH₂)₁₇ | 1(6) | Weak anti-HIV1 and HIV2 act. |
| 7. A | 2-(4-Fluorophenoxy)ethyl | NT | NT |

TABLE 1-continued

Structures A, B, C (pyrrolidine derivatives with R on N, CH2OH groups, and HO/OH substituents):

- A: HOCH2—[N-R pyrrolidine]—CH2OH with HO and OH (one stereochemistry)
- B: same connectivity, different stereochemistry
- C: same connectivity, different stereochemistry

| Structure | R | Inh. of Maltase(Sucrase) (%, at 100 mM) | HIV1/HIV2 Act. |
|---|---|---|---|
| 8. A:B 86/14 | 3-(4-Fluorophenoxy)propyl | 0(0) | No anti-HIV1 act. |
| 9. A | 4-Fluorophenyl | 0(0) | No anti-HIV1 act. |
| 10. B | 4-Fluorophenyl | 0(0) | No anti-HIV1 act. |
| 11. C | 4-Fluorophenyl | 19(18) | No anti-HIV1 act. |
| 12. A | 4,4-bis(4-Fluorophenyl)butyl | 20(30) | Weak anti-HIV1 act. |
| 13. A:B:C 88/6/6 | N-Ethoxycarbonyl-4-piperidinyl | 0(0) | No anti-HIV1 act. |
| 14. A | 3-[(3,4,5-Trimethoxybenzoyl)oxy]propyl | NT | NT |
| 15. A:B:C 57/39/4 | 3-Hydroxypropyl | 0(0) | NT |
| 16. A | nBu | 0(0) | NT |
| 17. A:B:C 76/12/12 | 2-(4-Fluorophenyl)ethyl | NT | No anti-HIV1 act. |
| 18. A | 2-(4-Methoxyphenyl)ethyl | NT | NT |
| 19. A | 3,3-(Diphenyl)-3-(cyano)propyl | NT | NT |
| 20. A | 2-Benzdioxolanylmethyl | NT | NT |
| 21. A | Cinnamyl | NT | NT |
| 22. A:B 86/14 | N-[3-(4-Fluorophenoxy)propyl]-cis-4-(3-methoxy)piperidinyl | 0(0) | No anti-HIV1 act. |
| 23. A | Ph2N | NT | NT |
| 24. A | (4-Fluorophenyl)amino | NT | NT |
| 25. B:C 68/32 | (4-Fluorophenyl)amino | NT | NT |
| 26. A:B or A:C 88/12 | Benzyloxy | NT | NT |

[1] At $10^{-3}$ M, there was 40% inhibition of maltase. At $10^{-4}$ M, there was 58% inhibition of lactose activity (at pH 5).
[2] At $10^{-3}$ M, there was 44% inhibition of lactose activity (at pH 5).
[3] Not Tested Compounds 6, 11 and 12 in Table 1 were screened at a single dose (100 micromolar) against sucrase and maltase, two glycosidase enzymes. In addition compounds 1 and 2 were screened at a dose of 1 mM. These compounds are described in Examples 6, 81 10, 11 and 12. The results of these tests indicate that compounds 1, 2, 6, 11 and 12 are glycosidase inhibitors and as a result may be useful in the treatment of diabetes in animals particularly humans. Compounds 1, 6 and 12 inhibited the growth of HIV-1 at high concentrations. Compounds 1, 2, 6 and 12 are novel compounds having glucitol stereochemistry. Compound 11 is likewise novel and it has the iditol stereochemistry.

The inhibition of maltase (sucrase) tests was carried out as recited hereinafter. Partially purified α-glycosidase was isolated from the rabbit's small intestine as described in the literature (B. L. Rhinehart et al. Life Sci. 1987, 41, 2325). The α-glycosidase activity was measured using maltase and sucrase as substrates. β-Glycosidase from almonds was obtained from Sigma (St. Louis), and β-glycosidase activity was measured using lactose as a substrate. The incubation mixture (200 μL) consisted of substrate (100 mM), enzyme, 100 mM NaCl, 0.1 mM Na2EDTA and either 10 mM MOPS (for pH 7), 10 mM maleic acid (for pH 6), or 10 Mm acetate (for pH 5) as buffer (adjusted to their respective pH with NaOH). Compounds dissolved in dimethylsulfoxide were added (final concentration of dimethylsulfoxide in the assay was 1%). The assay was performed at 37 deg C. for 30 minutes and arrested by incubation for 3 min at 85 deg C. After centrifugation for 2 min at 10,000 g, the supernatant was collected and processed for glucose determination. Glucose was measured with the hexokinase method (kit obtained from Boehringer Mannheim) on an EPOS 5060 EPPENDORF autoanalyser.

Anti-HIV-1 activity was tested in MT-4 cells as described previously (Pauwels et al. J. Virol Methods 1987, 11, 171). The cells were either infected with HIV-1 or mock infected and incubated in the presence of the test compounds. The number of viable cells was then determined after five days (Pauwels et al. J. Virol Methods 1988, 20, 309).

To prepare the pharmaceutical composition using the compounds of the invention, one or more compounds or salts thereof as the active ingredient are intimately mixed with a pharmaceutical carrier according to conventional pharmaceutical compounding techniques, which carrier may take a wide variety of forms depending on the form of preparation desired for administration, e.g., oral or parenteral. In preparation of oral dosage forms, any of the usual pharmaceutical media may be employed. Thus, for a liquid oral preparation, such as for example, suspensions, elixirs and solutions, suitable carrier and additives include water, glycols, oils, alcohols, flavoring agents, preservatives, coloring agents and the like. For solid preparations such as, for example, powders, capsules, and tablets, suitable carriers and additives include starches, sugars, diluents, granulating agents, lubricants, binders, disintegrating agents and the like. If desired, tablets may be sugar coated or enteric coated by standard techniques. For parenterals, the carrier will usually comprise sterile water, though other ingredients, for example, for the purposes such as aiding solubility or for preservation, may be included. Injectable suspensions may also be prepared, in which case appropriate liquid carriers suspending agents and the like may be employed. The pharmaceutical compositions herein will contain, per unit dosage, e.g., tablet, capsule, powder, injection, therapeutically effective amounts of the active ingredient for inhibiting glycosidase.

The following examples are intended to describe the preparation of various compounds according to the process of the present invention. They are to be considered representative of the chemistry employed and not to be considered limiting as to scope or kind.

Example 1

5-Keto-D-glucose (Formula V)

A suspension of 1,2-O-isopropylidene-α-D-glucofuranose (20.0 g, 0.091 mol) and dibutyltin oxide (24.9 g, 0.100 mol) in 500 mL of methanol was refluxed until the reaction mixture became clear (typically 30 minutes). After cooling, the solution was evaporated to dryness and the residue was dissolved in 1 L of methylene chloride. After the addition of tributyltin methoxide (41.7 g, 0.130 mol), the solution was cooled to 0° C., and a solution of bromine (20.8 g, 0.130 mol) in 60 mL of methylene chloride was added over 5 minutes. When the addition was complete, the reaction mixture was stirred another 5 minutes, and cyclohexene was added dropwise until the bromine color was discharged. The reaction mixture was then concentrated to a volume of 100 mL, and filtered. The filtrate was passed through a flash silica gel column (0–100% gradient of ethyl acetate in chloroform) to afford 8.2 g (41%) of 1,2-0-isopropylidene-5-keto-α-D-glucofuranose as a very pale green solid. The $^1$H NMR in CDCl$_3$ confirmed the structure. The sugar was dissolved in 100 mL of water, and 40 g of Dowex® 50W-X8 resin was added. The suspension was heated at 35° C. for 24 h and then cooled to ambient temperature. The resin was removed by filtration. Lyophilization of the filtrate afforded 7.02 g (96%) of the title compound as a cream-colored foam. The $^1$H NMR in D$_2$O indicated the product to be approximately 70% of the hydrated β-pyranose form of 5-keto-D-glucose in addition to other interconverting forms.

EXAMPLE 2

N-Benzhydryl-1-deoxynojirimycin (Formula VI)

To a −78° C. solution of 5-keto-D-glucose (Formula V, 4.00 g, 0.0225 mol) in 100 mL of methanol was added a cooled solution (−78° C.) of benzhydrylamine (3.29 g, 0.018 mol) and acetic acid (1.08 g, 0.018 mol) in 100 mL of methanol. Sodium cyanoborohydride (2.82 g, 0.0449 mole) was added, and the mixture was stirred at −78° C. for 2 h and then slowly warmed to ambient temperature. After 18 h, the solution was concentrated, saturated aqueous sodium carbonate was added, and the product was extracted into chloroform. The chloroform extracts were combined, dried (sodium sulfate), and concentrated to afford a yellow foam. Chromatographic purification on flash silica gel (5–10% gradient of methanol in chloroform) afforded 4.06 g (69%) of the title compound as a very pale yellow foam. $^1$H NMR and reversed-phase analytical HPLC showed that this substance was >95% stereochemically pure (ca. 4.5% of the iditol isomer). Recrystallization from MEOH afforded white needles, mp 101°–104° C. (corrected). Both $^1$H and $^{13}$C NMR in CDCl$_3$ and D$_3$CC(O)CD$_3$ confirmed the structure.

EXAMPLE 3

1-Deoxynojirimycin (Formula VII)

A mixture of N-benzhydryl-1-deoxynojirimycin as prepared in Example 2 (Formula VI, 1.00 g, 3.06 mmol) and 20% PD(OH)$_2$/carbon (0.20 g) in 40 mL of methanol was hydrogenated (60 psig) in a Parr apparatus for 24 h. The mixture was filtered through Celite, and the filtrate was concentrated to a light grey foam. The foam was washed with hexane and then dissolved in water (10 mL) and stirred over Dowex® 50W-X8 ion exchange beads for 2 h. The beads were washed with 1N aqueous NH$_4$OH solution until TLC analysis indicated the product had been completely removed from the resin. The combined ammonia washings were lyophilized to give 0.49 g (99%) of 1-deoxynojirimycin as a white foam, mp 198°–201° C. (literature mp 198°–202° C.: Kinast, G.; Schedel, M. *Angew. Chem. Int. Ed. Eng.* 1981, 20, 805). The 400-MHz $^1$H NMR spectrum of the material was identical to that of an authentic sample of 1-deoxynojirimycin (Sigma).

EXAMPLE 4

N-(2,2-Diphenylethyl)-1-deoxynojirimycin

To a cooled solution (−78° C.) of 2,2-diphenylethylamine (0.62 g, 3.14 mmol) and acetic acid (0.19 g, 3.14 mmol) in 18 mL of methanol was added a −78° C. solution of 5-keto-D-glucose (Formula V, 0.70 g, 3.93 mmol) in 18 mL of methanol. Sodium cyanoborohydride (0.49 g, 7.86 mmol) was added, and the mixture was stirred at −78° C. for 2 h and then slowly warmed to ambient temperature. After 18 h, the solution was concentrated, saturated aqueous sodium carbonate was added, and the solution was extracted with chloroform. The chloroform extracts were combined, dried (sodium sulfate), and concentrated to afford a yellow foam. Chromatographic purification on flash silica gel (5–7.5% gradient of methanol in chloroform) afforded 0.79 g (73%) of the title compound as a colorless form. Both $^1$H and $^{13}$C NMR in CDCl$_3$ and CD$_3$C(O)CD$_3$ confirmed the structure.

EXAMPLE 5

N-(Diphenylamino)-1-deoxynojirimycin (Formulas VIII and IX)

To a cooled solution (−78° C.) of 1,1-diphenylhydrazine hydrochloride (0.99 g, 4.49 mmol) in 25 mL of methanol was added a −78° C. solution of 5-keto-D-glucose (1.00 g, 5.61 mmol) in 25 mL of methanol. Sodium cyanoborohydride (0.71 g, 11.2 mmol) was added, and the mixture was stirred at −78° C. for 2 h and then slowly warmed to ambient temperature. After 18 h, the solution was concentrated, saturated aqueous sodium carbonate was added, and the solution was extracted with chloroform. The chloroform extracts were combined, dried (sodium sulfate), and concentrated to afford a yellow foam. Chromatographic purification on flash silica gel (5–7.5% gradient of methanol in chloroform) afforded 0.58 g (39%) of a 3:2 mixture (of the title compound (Formula VIII) as white plates and the corresponding iditol isomer (Formula IX) as a colorless foam. Both $^1$H and $^{13}$C NMR in CD$_3$C(O)CD$_3$ supported the structure.

EXAMPLE 6

N-Benzhydryl-2,5-anhydro-2,5-imino-D-glucitol (Formula XI)

A suspension of 5-keto-D-fructose (Formula X, 50 g, 0.28 mol; obtained from Chemical Dynamics) in 400 mL of MeOH was treated with sodium cyanoborohydride (40 g, 0.476 mol). A slurry of benzhydrylamine (42.0 mL, 0.234 mol) in 120-mL of MEOH was treated with sufficient acetic acid to bring the pH to 6-7 and then added over a 0.5 h period to the 5-keto-D-fructose (Formula X) and sodium cyanoborohydride suspension. An additional portion of sodium cyanoborohydride (20 g. 0.235 mol) was added and the mixture was stirred at reflux for 6 h. The solvent was then removed, and the residue treated with 10% sodium carbonate (ca. 100 mi), and the product was extracted into chloroform. The chloroform layers were dried (MgSO$_4$), filtered and concentrated to give a tacky yellow solid. This was purified on two Waters Prep 500 columns (CHCl$_3$/MeOH/NH$_4$OH, 88:11:1) to give ca. 50 g of the target compound. Recrystallization from ethyl acetate gave 21.3 g (28%) of white needles, 152.5°-154.5° C. (corrected). Both $^1$H and $^{13}$C NMR in CDCl$_3$ supported the assigned structure.

Elemental Analysis: Calculated for C$_{19}$H$_{32}$NO$_4$: C, 69.28; H, 7.04; N, 4.25; O, 19.43. Found: C, 69.21; H, 7.03; N, 4.19; O, 19.61.

EXAMPLE 7

N-Benzhydryl-2,5-anhydro-2,5-imino-D-mannitol (Formula XII)

In Example 6, two other stereoisomers were produced. Compound of Formula XII (R$^3$=Ph$_2$ CH) was obtained separately during the chromatography described in Example 6, and then rechromatographed and recrystallized from MEOH/CH$_2$Cl$_2$/pentane to give 0.7 g white crystals, 172°-179° C. (corrected). Both $^1$H and $^{13}$C NMR in CDCl$_3$ supported the assigned structure.

Elemental Analysis: Calculated for C$_{19}$H$_{23}$NO$_4$: C, 69.28; H, 7.04; N, 4.25; O, 19.43. Found: C, 68.79; H, 7.00; N, 4.14; O, 19.45.

EXAMPLE 8

2,5-Anhydro-2,5-imino-D-glucitol (Formula XIV)

A mixture of N-benzhydryl-2,5-anhydro-2,5-imino-D-glucitol (Formula XI, R$^3$=Ph$_2$CH 8.40 g, 25.5 mmol) and 0.42 g of 20% PD(OH)$_2$/carbon in 100 mL of MeOH was set shaking on a Parr apparatus under 60 psig of hydrogen overnight. This solution was then filtered and concentrated. Hexane (ca. 300 mi) was added, and the solvent was then removed from a white solid, which was washed with ca. 200 mL of hexane. The product was recrystallized from ETOH/CH$_3$CN to give 3.79 g (91%) of white needles, mp 139°-142.50° C. (corrected). Both $^1$H and $^{13}$C NMR in D$_2$O supported the assigned structure.

Elemental Analysis: Calculated for C$_6$H$_{13}$ NO$_4$: C, 44.17; H, 8.03; N, 8.58; O, 39.22. Found: C, 44.21; H, 8.13; N, 8.54; O, 38.94.

EXAMPLE 9

N-2-(4-Fluorophenoxy)ethyl-2,5-Anhydro-2,5-imino-D-glucitol

A solution of a compound Formula XIV (2.60 g, 0.0159 mol), 2-(4-fluorophenoxy)ethyl bromide (3.70 g, 0.0169 mol), and Na$_2$CO$_3$ (1.86 g, 0.0175 mol) in 11 mL of dimethylformamide was heated at 85° C. for 8 h. The solution was cooled, then treated with 250 mL of ethyl ether portion wise, and the solvent was removed. The resultant residue was diluted with chloroform, filtered, and concentrated. This crude material was chromatographed on a Waters Prep-500 HPLC (88:11:1, CHCl$_3$/MEOH/NH$_4$OH) to give the product, which was recrystallized from EtOAc/hexane (3.49 g, 73%), mp 96°-98° C. (corrected). $^1$H NMR supported the assigned structure.

Elemental Analysis: Calculated for C$_{14}$H$_{20}$FNO$_5$: C, 55.81; H, 6.69; N, 4.65; F, 6.31. Found: C, 55.78; H, 6.71; N, 4.55; F, 6.55.

EXAMPLE 10

N-(4-Fluorophenyl)-2,5-anhydro-2,5-imino-D-glucitol (Formula XVI) and isomers A solution of 4-fluoroaniline (30 g, 0.27 mol) and 15.46 mL of HOAC in 100 mL of MEOH was added to 5-keto-D-fructose (57.7 g, 0.324 mol) in 350 mL of MEOH. To this suspension was added 32 g of NaCNBH$_3$ (0.5 mol). The tan mixture was heated at reflux. After reacting overnight, the solution was cooled, the MeOH was largely evaporated and the residue was dissolved in ca. 200 ml. of water and treated with ca. 500 mL of Dowex 50W-X8 cation exchange resin. After stirring for 2 h, the resin and solution were added to a column with a bed of 150 mL more resin, and the supernatant was eluted. The resin was then washed with another ca. 500 mL of water. The column was then eluted with 1N NH$_4$OH, and the water of the fractions containing the products was removed under reduced pressure. The residue was purified on two Waters Prep 500.HPLC columns (hexane/iPrOH/NH$_4$OH, 65:34:1) to give fractions highly enriched in all three stereoisomers. The fastest eluting material was recrystallized from iPrOH/hexane to give 4.9 g white needles (7%) of the mannitol isomer (Formula XVII). Both C-13 and H-1 NMR are consistent with the assigned structure. M.p. 198° C. (browning), 205°-207° C.; (melting with decomposition).

Elemental Analysis: Calculated for C$_{12}$H$_{16}$ FNO$_4$: C, 56.03; H, 6.27; N, 5.44; F, 7.38. Found C, 56.12; H, 6.37; N, 5.26; F, 7.18.

The middle eluting component was recrystallized twice from iPrOH/hexane to give >99% stereochemically pure glucitol isomer (Formula XVI; 4.9 g, 7%), m.p. 140.5°-142° C. Both H-1 and C-13 NMR are consistent with the assigned structure.

Elemental Analysis: Calculated for C$_{12}$H$_{16}$FNO$_4$: C, 56.03; H:, 6.27; N, 5.44; F, 7.38. Found: C, 55.901, H, 6.21; N, 5.32; F, 7.37.

The slowest eluting component was recrystallized from iPrOH/hexane to give a 1.45 g (2%) of ca. 98% stereochemically pure iditol isomer (Formula XVIII; entry 11 of Table). Both H-1 and C-13 NMR are consistent with the assigned structure.

Elemental Analysis: Calculated for C$_{12}$H$_{16}$ FNO$_4$: C, 56.03; H, 6.27; N, 5.44; F, 7.38. Found: C, 56.04; H, 6.36; N, 5.34; F, 7.23.

EXAMPLE 11

N-Stearyl-2,5-anhydro-2,5-imino-D-glucitol (Entry 6 of Table)

A suspension of stearyl amine (11.0 g, 40.8 mmol) in 300 mL of MEOH was treated with acetic acid (2.34 mL, 40.9 mmol), and then heated at reflux to effect dissolution. The solution was cooled to ambient temperature, and then treated with Formula X (8.7 g, 49.1 mmol) and NaCNBH$_3$ (5.22 g, 81.6 mmol). The mixture was allowed to reflux overnight. Most of the MEOH was evaporated and ca. 100 mL of 10% aqueous Na$_2$CO$_3$ was added. The product was extracted into 2×200 mL of methylene chloride which were dried (MgSO$_4$), filtered, and concentrated to a yellow oil. This was purified on two Waters Prep-500 HPLC columns (CHCL$_3$/MEOH/NH$_4$OH, 88:11:1). One of the purer fractions was recrystallized from MeOH/water to give a buff-colored solid. Both H-1 and C-13 NMR are consistent with the assignment as an 88:12 mixture of the glucitol/mannitol isomers, m.p. 85°–93° C.

Elemental Analysis: Calculated for C$_{24}$H$_{49}$NO$_4$: C, 69.35; H, 11.88; N, 3.37; O, 15.40. Found: C, 68.84;, H, 11.92; N, 3.29; O, 15.35.

EXAMPLE 12

N-[4,4-bis(4-Fluorophenyl)butyl]-2,5-anhydro-2,5-imino-D-glucitol tosylate (Entry 12 of the Table)

A suspended solution of compound Formula XIV (2.53 g, 0.0155 mol), 4,4-bis(4-fluorophenyl)butyl chloride (5.34 g, 0.0165 mol), KI (2.83 g, 0.017 g), and K$_2$CO$_3$ (2.35 g, 0.017 g) in 15 mL of DMF was heated at 90° C. for 18 h. After 18 h, an additional 0.31 g of the alkyl chloride was added, and reaction stirred for 24 more h. The reaction mixture was then poured into 200 mL of water and the supernatant was decanted from a brown oil. The product was purified by high-pressure liquid chromatography (CHCl$_3$/MEOH/NH$_4$OH, 78:21:3). The free base was converted to a tosylate salt and crystallized from iPrOH/ether. The H-1 NMR supports the assigned structure, m.p. 166°–167° C.

Elemental Analysis: Calculated for C$_{22}$H$_{27}$F$_2$NO$_4$·C$_7$H$_8$O$_3$S; C, 60.09; H, 6.09; N, 2.42; F, 6.56; S, 5.53. Found: C, 59.99; H, 6.06; N, 2.30; F, 6.58; S, 5.38.

EXAMPLE 13

N-Butyl-1-deoxynojirimycin

To a cooled solution (−78° C.) of n-butylamine (0.26 g, 3.50 mmol) and acetic acid (0.21 g, 3.50 mmol) in 19.5 mL of methanol was added a −78° C. solution of 5-keto-D-glucose (0.78 g, 4.38 mmol) in 19.5 mL of methanol. Sodium cyanoborohydride (0.55 g, 8.76 mmol) was added, and the mixture was stirred at −78° C. for 2 h and then slowly warmed to ambient temperature. After 24 h, the solution was concentrated to a beige foam which was dissolved in 10 mL of methanol and stirred over Dowex beads (5 g). The column was washed with water and then with 1N NH$_4$OH solution. The fractions containing product were combined and lyophilized. Chromatographic purification on flash silica gel (14–29% gradient of methanol in chloroform with 1% conc. aqueous NH$_4$OH) afforded 0.42 g (55%) of the title compound (glucitol isomer) as a buff-colored solid and 0.02 g (2%) of the iditol isomer. Both $^1$H and $^{13}$C NMR in D$_2$O were consistent with the assigned structure.

What is claimed is:

1. A method for the synthesis of a compound of the formula I and stereoisomers thereof;

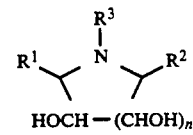

HOCH—(CHOH)$_n$ wherein n=1 and R$^1$ and R$^2$ are the same or different and are selected from the group consisting of CH$_2$OH, CH$_3$H, and CH$_2$F; wherein R$^3$ is selected from the group consisting of H, straight and branched C$_1$–C$_{20}$ alkyl, substituted straight and branched C$_1$–C$_{20}$ alkyl, aralkyl, phenyl, substituted phenyl, heteroaryl, alkyl amino, aryl amino, amino, alkyl oxy and aralkyl oxy, with the proviso that R$^3$ cannot be a group such that a carbon atom attached to the ring nitrogen is a quaternary carbon atom, which comprises reacting a compound of the formula II:

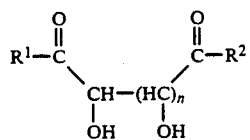

wherein n=1 or 2; with an amine of the formula R$^3$NH$_2$; said reaction being carried out in the presence of an acid and a source of hydride.

2. The method of claim 1, wherein the hydride source is a complex borohydride.

3. The method of claim 2, wherein the complex borohydride is any of NACNBH$_3$, nBu$_4$NCNBH$_3$, catecholborane or mixtures thereof.

4. The method of claim 1, wherein the straight or branched C$_1$–C$_{20}$ alkyl is substituted with any of hydroxy, alkoxy, thio, carboxy, or dialkylamino.

5. The method of claim 1, wherein R$^3$ is hydrogen, n-butyl, or 2-hydroxyethyl.

6. The method of claim 1, wherein the phenyl is substituted with one or more groups selected from alkyl, alkoxy, halogen, carboxy, thio or alkythio.

7. The method of claim 1, wherein the amine is selected from any of ammonia, hydrazine, benzhydrylamine, benzylamine or aniline.

8. The method of claim 1, wherein the amine contains more than 12 carbon atoms.

9. The method of claim 1, wherein the amine is a primary amine.

10. The method of claim 1, wherein the acid is a mineral or organic acid.

11. The method of claim 10, wherein the acid is selected from any one of HCl, HBr and HI.

12. The method of claim 1, further comprising, when R$^3$ is other than H, replacing the R$^3$ group with H by carrying out hydrogenolysis on the compound of formula II.

13. The method of claim 1, further comprising, when R$^3$ is H, reacting the compound of formula I with a compound of the formula R$^4$X, wherein R$^4$ is any of alkyl, aralkyl, dialkylamino alkyl or alkoxy- or hydroxy-alkyl and X is any of Cl, Cr, I, tosylate, or mesylate.

* * * * *